US012447038B2

(12) United States Patent
Rugfelt

(10) Patent No.: US 12,447,038 B2
(45) Date of Patent: Oct. 21, 2025

(54) METHOD FOR FILLING A FLEXIBLE ELEMENT FOR SUPPORTING AND STABILIZING AN INJURED PERSON

(71) Applicant: KOHLBRAT & BUNZ Gesellschaft m.b.H., Radstadt (AT)

(72) Inventor: Haakan Rugfelt, Radstadt (AT)

(73) Assignee: KOHLBRAT & BUNZ GESELLSCHAFT M.B.H., Radstadt (AT)

( * ) Notice: Subject to any disclaimer, the term of this patent is extended or adjusted under 35 U.S.C. 154(b) by 345 days.

(21) Appl. No.: 17/873,764

(22) Filed: Jul. 26, 2022

(65) Prior Publication Data

US 2023/0029246 A1 Jan. 26, 2023

Related U.S. Application Data

(63) Continuation of application No. PCT/AT2020/060428, filed on Dec. 1, 2020.

(30) Foreign Application Priority Data

Jan. 28, 2020 (AT) .............................. A 50064/2020
Mar. 10, 2020 (AT) .............................. A 50194/2020

(51) Int. Cl.
*A61F 5/058* (2006.01)

(52) U.S. Cl.
CPC ................................ *A61F 5/05833* (2013.01)

(58) Field of Classification Search
CPC .... A61F 5/00; A61F 5/04; A61F 5/05–05825; A61F 5/05833; A61F 5/05841–05891; B65B 1/04; B65B 1/16; B65B 1/18
See application file for complete search history.

(56) References Cited

U.S. PATENT DOCUMENTS 1,782,733 A * 11/1930 Lilly .......................... B65B 1/18 141/315
2,260,302 A * 10/1941 Driscoll ..................... B65B 1/18 222/413
3,212,497 A * 10/1965 Dickinson ............ A61B 6/0421 128/DIG. 20
5,595,806 A * 1/1997 Korfmacher ........... B65D 81/09 229/87.01

(Continued)

FOREIGN PATENT DOCUMENTS

AT 510555 A4 * 5/2012 ......... A61F 5/05833
CN 1665461 9/2005

(Continued)

OTHER PUBLICATIONS

International Search Report issued Feb. 23, 2021 in International (PCT) Application No. PCT/AT2020/060428.

*Primary Examiner* — Michelle J Lee
(74) *Attorney, Agent, or Firm* — Wenderoth, Lind & Ponack, L.L.P.

(57) ABSTRACT

A method is provided for filling a flexible element with a loose granular material, wherein the element has two lengths of material connected to each other at points in the interior and along the edge, and includes leaving a filling opening. An air pressure difference between the interior and the external environment is generated, which widens the interior before it is filled with the granular material.

11 Claims, 2 Drawing Sheets

(56) References Cited

U.S. PATENT DOCUMENTS

| | | | |
|---|---|---|---|
| 5,682,929 | A | 11/1997 | Maginot et al. |
| 2009/0166935 | A1 | 7/2009 | Jacob et al. |
| 2010/0012220 | A1 | 1/2010 | Waldron et al. |

FOREIGN PATENT DOCUMENTS

| | | |
|---|---|---|
| CN | 2868247 | 2/2007 |
| CN | 101472732 | 7/2009 |
| CN | 201789975 | 4/2011 |
| CN | 103261822 | 8/2013 |
| DE | 195 26 743 | 1/1997 |
| EP | 2 130 769 | 12/2009 |
| EP | 3 581 500 | 12/2019 |
| JP | 11-236012 | 8/1999 |
| WO | 2013/044277 | 4/2013 |

* cited by examiner

Fig. 2
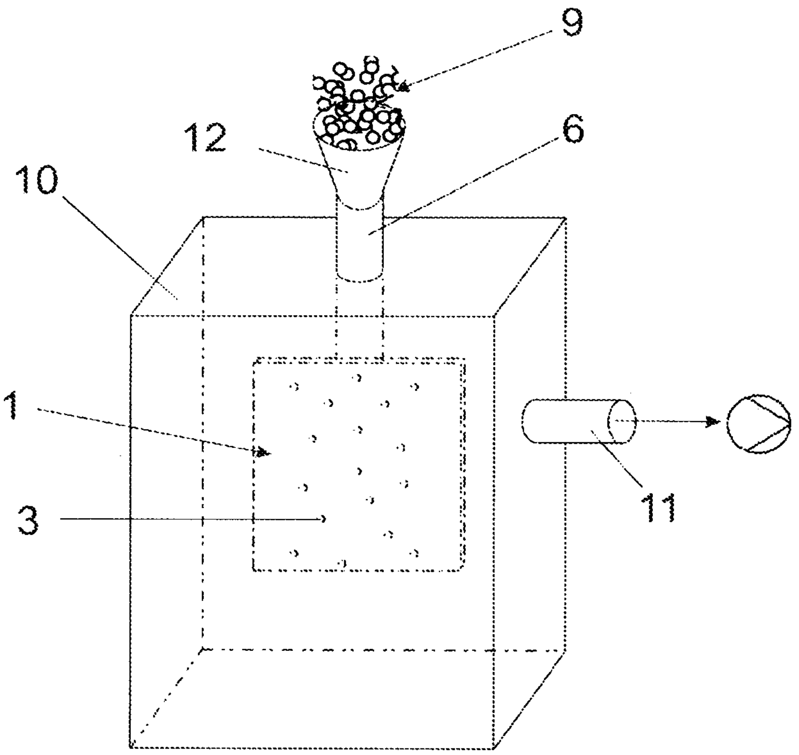
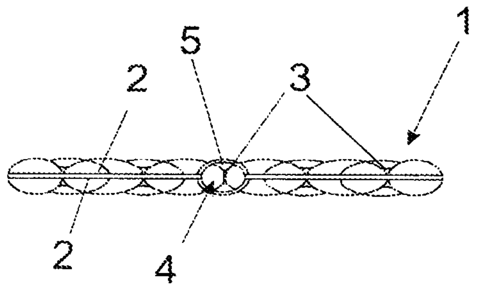
Fig. 3

METHOD FOR FILLING A FLEXIBLE ELEMENT FOR SUPPORTING AND STABILIZING AN INJURED PERSON

BACKGROUND OF THE INVENTION

The invention relates to a method for filling a flexible element, for example for supporting and stabilizing an injured person, with a loose granular material, and the element has two lengths of material connected to each other along the edge at points in the interior and leaving a filling opening.

Stabilizing devices, also referred to as vacuum mattresses and vacuum splints, for transporting and immobilizing injured persons, have a shell made of an air-tight plastic film and a uniform filling made of a plastic granular material, in particular polystyrene foam balls. These stabilizing devices can be evacuated by a suction pump after they have been fitted to and fixed on a body part to be immobilized. This leads to a tight packing of the loosely poured-in granular material and thus to a stiffening of the flexible element, which in this way forms a substantially rigid sleeve. For fixing the stabilizing device on the body part in a manner which is as universal as possible, fastening belts are arranged in the circumferential direction of the body part and provided with conventional adjustable connecting fittings. As a uniform distribution of the granular material has to be achieved, vacuum mattresses and splints are primarily suitable for a horizontal use position. When used in a non-horizontal position, for example in the case of seated injured persons, there is a danger that the filling forms a thinner layer, or is even missing, in a higher area because it has shifted from the top to the bottom during handling.

A method for producing such a stabilizing device is known from WO 2013/044277, in which the two films are connected to each other along the edge on three sides and inside in a four-point grid such that channels remain parallel to at least one side edge. During the filling with granular material, a filling lance is inserted into each channel and granular material is supplied through the filling lances, and the filling lances are pulled out again as the filling progresses. Finally, the films are then also connected to each other at the open upper transverse edge. The internal connections are provided in order to guarantee an approximately uniform distancing of the two films over the entire surface area and thus an approximately identical layer thickness of the granular material.

SUMMARY OF THE INVENTION

The object of the invention is to simplify the filling method for an element of a stabilizing device, wherein the internal connections can also be produced irrespective of a particular shape and a particular grid pattern.

This is achieved according to the invention in that an air pressure difference between the interior and the external environment is generated, which widens (expands) the interior of the element before it is filled with the granular material.

In principle, it is possible to reduce the air pressure outside or to increase it inside, or to use both measures at the same time. Preferably, the element is introduced into a vacuum chamber, the filling opening is accessible from the outside, and the vacuum, which widens the interior of the element, is generated in the vacuum chamber.

In a preferred embodiment, the filling opening is provided in a fill nozzle formed of areas of the two lengths of material, and the filling opening is closed after the granular material has been introduced. It is furthermore preferable that the element is suspended from the fill nozzle in the vacuum chamber, wherein its opening protrudes externally.

The filling with the granular material is preferably effected by gravity after or at the same time as the widening of the interior by suctioning off the ambient air. If air is blown into the interior, however, the granular material can also already be added to the air.

The flexible element can be formed of two air-tight films, at least one of which has a valve in order to evacuate the element after it has been fitted to the injured person. However, it is also possible to use lengths of an air-permeable non-woven material or the like, which are enclosed between two air-tight films after the filling, at least one of which has the above-mentioned valve. Thus, the shell containing the filled element can then be evacuated after it has been fitted to the injured person.

The filling consists above all of a granular material made of foamed polystyrene with a weight of between 20 kg/m$^3$ and 70 kg/m$^3$, in particular 60 kg/m$^3$, with the average diameter of the individual particles being between 0.4 mm and 5 mm, in particular between 0.5 mm and 2 mm. The mesh width or pore size of the air-permeable material web is of course smaller than the diameter of the particles. As a result, the air resistance that is necessary for achieving the pressure difference between the interior and the environment is also ensured.

BRIEF DESCRIPTION OF THE DRAWINGS

The invention will now be described in more detail below with reference to the drawings, without being limited thereto, wherein:

FIG. 2 is a schematic representation of the filling of the element with granular material, and FIG. 3 is a schematic top view of the element during the filling operation.

DETAILED DESCRIPTION OF THE INVENTION

Figure 1:
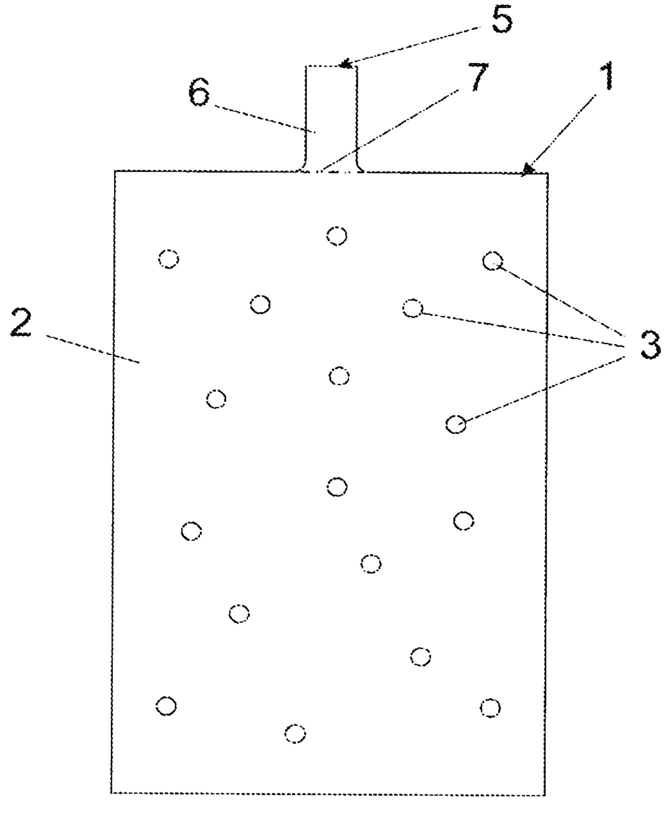
FIG. 1 is a schematic view of a rectangular element.

An element 1 which, depending on the size and shape, is suitable for immobilizing and stabilizing an injured body part, for example a broken arm or leg, or an injured person, has two lengths of material 2 made of an air-tight plastic, for example a polyurethane, or an air-permeable non-woven material, which are connected to each other, in particular welded, circumferentially along the edge and at suitable weld points 3 inside.

The interior 4 contains a granular material 9 made of a lightweight plastic, in particular a foamed polystyrene, and the diameter of the individual balls lies between 0.4 mm and 5 mm, in particular between 0.5 mm and 2 mm. The granular material is made of foamed polystyrene with a weight in a range between 20 kg/m$^3$ and 70 kg/m$^3$, in particular 60 kg/m$^3$. The mesh width or pore size of the air-permeable material web is of course smaller than the diameter of the particles. One of the two films is provided with a valve, not shown, via which the air enclosed inside can be suctioned off, as a result of which the granular material 9 which is loosely poured in and can be displaced or shifted by external action is made tightly packed, which stiffens the element 1 enough to prevent a movement of the injured body or body part.

As shown in FIG. 1, such an element 1 is produced as follows: first of all two lengths of material 2 are cut to size, which in each case have an extension (protrusion). The two lengths of material 2 are laid one on top of the other and welded together, at several connection points 3 spaced apart from each other, directly or by spacers inside and along the edge, leaving a filling opening 5. The two extensions complement each other to form a fill nozzle 6 having the filling opening 5, with the result that an open sack-like structure is formed. The arrangement of the (weld) connection points 3 is not subject to a particular pattern, and can be chosen according to practical circumstances, depending on the intended use.

FIG. 2 schematically shows a vacuum chamber 10, the interior of which is connected to a vacuum generator via a suction connection 11. The vacuum chamber 10 has an upper opening. The element 1 is now introduced into the vacuum chamber 10, and the fill nozzle 6 formed by the extensions (protrusions) of the lengths of material 2 is guided through the upper opening of the vacuum chamber outwardly sealed. The filling opening 5 is therefore outside the vacuum chamber 10 and is under standard pressure. Above the fill nozzle 6, a schematically shown filling funnel 12 is provided, via which granular material 9 can in particular be supplied by gravity. A vacuum is now generated in the vacuum chamber 10, due to which the two lengths of material 2 are pulled apart from each other. The result is that the interior 4 of the element 1, which is under standard pressure, increases in size, as schematically represented in FIG. 3, and granular material 9 flows into the interior 4 until the required quantity is achieved. The filling is distributed without difficulty between the connection points 3.

The filled element 1 is then removed from the vacuum chamber 10, and the filling opening 5 is sealed, in particular by a seam between the two lengths of material along the seam line 7 shown dot-dashed in FIG. 1. The two extensions (protrusions), which are no longer required, of the lengths of material 2 are then preferably cut off. The element 1 is ready for use if air-tight plastic films are used as lengths of material. If the lengths of material consist of an air-permeable plastic non-woven or the like, then the filled element is finally enclosed in a shell consisting of two air-tight plastic films, which can then in turn be evacuated to stiffen the element 1.

The invention claimed is:

1. A method for filling an air-tight flexible element for supporting and stabilizing an injured person with a loose granular material, the air-tight flexible element having two lengths of material connected to each other at points in an interior of the air-tight flexible element and along an edge of the air-tight flexible element, leaving a filling opening, the method comprising:

placing the air-tight flexible element within a vacuum chamber such that the filling opening extends through a first location of the vacuum chamber and is accessible outside of the vacuum chamber;

after placing the air-tight flexible element within the vacuum chamber, generating an air pressure difference between the interior of the air-tight flexible element and an external environment of the air-tight flexible element so as to expand the interior of the air-tight flexible element, the air pressure difference being generated by creating a vacuum within the vacuum chamber via a suction connection communicating with an interior of the vacuum chamber at a second location of the vacuum chamber to suction off ambient air from within the vacuum chamber, the second location of the vacuum chamber being spaced apart from the first location such that a suction stream from the suction connection does not directly communicate with a filling stream of the granular material entering the air-tight flexible element, and after generating the air pressure difference between the interior of the air-tight flexible element and the external environment of the air-tight flexible element, filling the expanded interior of the air-tight flexible element through the filling opening with the granular material consisting of foamed polystyrene having a weight in a range between 20 $kg/m^3$ and 70 $kg/m^3$ to support and stabilize the injured person.

2. The method according to claim 1, wherein the generating of the air pressure difference between the interior of the air-tight flexible element and the external environment of the air-tight flexible element further includes blowing air into the interior of the air-tight flexible element through the filling opening.

3. The method according to claim 2, wherein the filling of the expanded interior includes adding the granular material to the air blown into the interior through the filling opening.

4. The method according to claim 1, wherein the filling opening comprises a fill nozzle formed of portions of the two lengths of material and extending through the vacuum chamber, and a filling funnel at a distal end of the fill nozzle outside of the vacuum chamber, the method further comprising closing the filling opening after the filling of the expanded interior of the air-tight flexible element with the granular material.

5. The method according to claim 4, wherein the air-tight flexible element is suspended from the fill nozzle in the vacuum chamber.

6. A method for producing an air-tight flexible element for supporting and stabilizing an injured person, the method including using the method for filling the air-tight flexible element according to claim 1.

7. The method according to claim 6, further comprising forming the two lengths of material of air-tight films, at least one of the two lengths having a valve so that air within the air-tight flexible element filled with the granular material can be evacuated after the air-tight flexible element has been fitted to the injured person.

8. The method according to claim 6, further comprising:

forming the two lengths of material of an air-permeable non-woven material to form an intermediate flexible element, and after filling the intermediate flexible element with the granular material, enclosing the intermediate flexible element in a shell consisting of air-tight films to form the air-tight flexible element, at least one of the air-tight films having a valve so that air within the shell containing the air-tight flexible element can be evacuated after the shell has been fitted to the injured person.

9. The method according to claim 1, wherein the filling of the expanded interior includes introducing the granular material through the filling opening by gravity after the generating of the air pressure difference to expand the interior.

10. The method according to claim 1, wherein each particle of the granular material has a diameter in a range between 0.4 mm and 5 mm.

11. The method according to claim 1, wherein the granular material consists of foamed polystyrene having a weight of 60 $kg/m^3$, and each particle has a diameter in a range between 0.5 mm and 2 mm.

* * * * *